United States Patent
Kikuchi

Patent Number: 5,993,893
Date of Patent: Nov. 30, 1999

[54] EVALUATION METHOD FOR POLYCRYSTALLINE SILICON FILM

[75] Inventor: Masaharu Kikuchi, Tokyo, Japan

[73] Assignee: NEC Corporation, Tokyo, Japan

[21] Appl. No.: 09/025,668

[22] Filed: Feb. 19, 1998

[30] Foreign Application Priority Data

Feb. 19, 1997 [JP] Japan ................................ 9-034921

[51] Int. Cl.$^6$ .................................................. B05D 5/12
[52] U.S. Cl. .................... 427/8; 427/255.18; 427/255.7; 427/372.2; 438/488; 438/764
[58] Field of Search ........................ 427/8, 248.1, 255.18, 427/255.7, 372.2; 438/764, 488

[56] References Cited

FOREIGN PATENT DOCUMENTS 6-260544  9/1994  Japan .

Primary Examiner—Roy V. King
Attorney, Agent, or Firm—Sughrue, Mion, Zinn, Macpeak & Seas, PLLC

[57] ABSTRACT

The invention provides an evaluation method for a polycrystalline silicon film by which the film quality of a polycrystalline silicon film can be evaluated by a simple method. A silicon oxide film is formed on a p-type silicon substrate, and a photo-resist film having two openings therein is formed on the silicon oxide film. The silicon oxide film is etched to form openings therein, and a polycrystalline silicon film is deposited. Then, arsenic is ion implanted, and heat treatment is performed to form a diffused layer. The polycrystalline silicon film is patterned to form polycrystalline silicon electrodes. A voltage is applied between the polycrystalline silicon electrodes to measure a withstanding voltage and a condition of the diffused layer is recognized, and evaluation of the film quality of the polycrystalline silicon film and an interface condition between the polycrystalline silicon film and the p-type silicon substrate is performed based on the recognition.

6 Claims, 7 Drawing Sheets

As I/I

EVALUATION METHOD FOR POLYCRYSTALLINE SILICON FILM

BACKGROUND OF THE INVENTION

1. Field of the Invention

This invention relates to an evaluation method for a polycrystalline silicon film formed using a low pressure chemical vapor deposition (LPCVD) method or a like method.

2. Description of the Related Art

Conventionally, since a simple method for a film quality of a polycrystalline silicon film has not been available, in-line evaluation of a film quality of a polycrystalline silicon film has not been performed in a manufacturing process of semiconductor devices. However, it is widely known that the film quality of a polycrystalline silicon film has a significant influence on the characteristics of a semiconductor device. For example, in a manufacturing process of a bipolar transistor, a polycrystalline silicon film, for example, of the n type is formed on a base region and heat treatment is performed to form an n-type emitter diffusion layer. Since difference in particle size of polycrystalline silicon, interface condition with a substrate and so forth makes the diffusion rate of an impurity different, the emitter diffusion layer is formed in different junction depth and consequently in different base width (height).

Conventionally, a device is produced and a characteristic of the device is evaluated to indirectly effect evaluation of a polycrystalline silicon film which has been used to produce the device. This evaluation method is described with reference to FIGS. 4(a) to 4(e) taking a bipolar transistor as an example.

First, as seen in FIG. 4(a), an n$^+$-type buried layer 12 is formed on a p-type silicon substrate 11 applying a photo-lithography method, a thermal diffusion method and so forth, and an n-type epitaxial layer 13 is grown using a reduced pressure epitaxial growth method or the like. Then, as shown in FIG. 4(b), a base diffused layer 14 is formed applying a photo-lithography method and an ion implantation method or the like, and similarly, a collector lead diffused layer 15 is formed applying a photo-lithography method and an ion implantation method or the like similarly, whereafter a silicon oxide film 16 is grown on the n-type epitaxial layer 13, base diffused layer 14 and collector lead diffused layer 15 using a CVD method or the like. Then, in an emitter formation region, an emitter opening 17 is formed using a photo-lithography method and a dry or wet etching method. Thereafter, as shown in FIG. 4(c), a polycrystalline silicon film 18 is grown using an LPCVD method, and an n-type impurity such as, for example, arsenic (As) is ion implanted over the entire area of the polycrystalline silicon film 18.

Then, as shown in FIG. 4(d), the polycrystalline silicon film 18 is patterned so as to cover over the emitter opening 17 using a photo-lithography method and a dry etching method, and in order to isolate a transistor and wiring lines, an inter-layer insulating film 19 in the form of a silicon oxide film or the like is grown on the polycrystalline silicon film 18 using a CVD method. Thereafter, heat treatment is performed around 900° C. to diffuse As in the polycrystalline silicon film 18 in the emitter opening 17 into the base diffused layer 14 to form an emitter diffused layer 20. Finally, as shown in FIG. 4(e), contact openings for electrodes are formed above the base diffused layer 14, emitter diffused layer 20 and collector lead diffused layer 15 using a photo-lithography method and a dry or wet etching method, and a layer of an electrode material such as aluminum is formed by a sputtering method and then patterned using a photo-lithography method and a dry etching method to form a base electrode 21, an emitter electrode 22 and a collector 23.

Then, the emitter electrode 22 is connected to the ground potential while the base electrode 21 and the collector 23 are connected to a positive potential, and a value (current amplification factor=hFE) is calculated by dividing a current flowing through the collector electrode 23 by a current flowing through the base electrode 21 then to measure a characteristic of the transistor. Here, if the value hFE is within a predetermined range, then it is determined that the polycrystalline silicon film is formed in a normal state. In any other case, it is estimated that the film quality of the polycrystalline silicon film is defective, and evaluation of the film quality is performed and a countermeasure is taken. For the evaluation of the film quality, a transmission electron microscope (TEM) is used in most cases. In particular, a polycrystalline silicon film is cut into a thin piece, and the thin piece is mounted in position on a transmission electron microscope to observe the crystal structure of it.

Where the method wherein a device is produced and a characteristic of the device is measured to evaluate a polycrystalline silicon film is employed, since all steps for manufacture of the device must be completed, much time is required until evaluation of the film quality becomes possible. Further, since the characteristic of the device is varied also by a factor other than the film quality of the polycrystalline silicon, accurate evaluation is difficult with the evaluation method.

Further, where a transmission electron microscope is used for evaluation of the film quality of a polycrystalline silicon film, it is very cumbersome and requires many man-hours to produce a specimen for the evaluation, and much time is required until observation for particle sizes becomes possible. Furthermore, a correlation between a result of observation and an actual device characteristic cannot be discriminated clearly, and besides, integrated evaluation of polycrystalline silicon including an interface condition between the polycrystalline silicon and a silicon substrate cannot be performed.

SUMMARY OF THE INVENTION

It is an object of the present invention to provide an evaluation method for a polycrystalline silicon film by which the film quality of a polycrystalline silicon film can be evaluated and discriminated in a short time on the manufacturing line level and production of a defective semiconductor device which arises from a polycrystalline silicon film can be prevented.

In order to attain the object described above, according to the present invention, there is provided an evaluation method for a polycrystalline silicon film, which comprises a first step of forming an insulating film on a silicon substrate and forming an opening in the insulating film, a second step of depositing a polycrystalline silicon film on the overall area of the insulating film, a third step of doping the polycrystalline silicon film with an impurity and performing heat treatment to form a diffused layer in a surface region of the silicon substrate through the polycrystalline silicon film in the opening of the insulating film, and a fourth step of evaluating the diffused layer formed by the third step thereby to evaluate a film quality of the polycrystalline silicon film.

Preferably, after the third step, the polycrystalline silicon film is patterned to form a pair of electrodes which contact with the diffused layer, and in the fourth step, an electric resistance of the diffused layer is measured making use of the electrodes, or alternatively, in the first step, a pair of openings are formed in the insulating layer, and after the third step, the polycrystalline silicon film is patterned to form a pair of electrodes which contact with different pieces of the diffused layer, and then in the fourth step, a withstanding voltage between the different pieces of the diffused layer is measured.

While the evaluation method of the present invention can be worked using a monitor wafer, it can be performed also on a wafer on which a product chip is formed. In the latter case, the first to fourth steps are used also as steps of manufacturing a product chip, and the opening is formed on the product chip or a scribe line.

The evaluation method may be constructed such that openings of a same pattern or different patterns are formed in different regions on the same wafer, and a film quality of the polycrystalline silicon film is evaluated for the plurality of different regions.

The evaluation method for a polycrystalline silicon film of the present invention makes use of the fact that, even if heat treatment conditions are same, the diffusion rate of an impurity in a polycrystalline silicon film is different depending upon the crystal particle size of the polycrystalline silicon film and the interface condition of the polycrystalline film with a lower layer film. In particular, by diffusing an impurity partially into the silicon substrate as such lower layer film and measuring a diffusion resistance or a withstanding voltage of the impurity diffused portion of the silicon substrate, a condition of the diffused layer can be recognized, and the film quality of the polycrystalline silicon film can be evaluated based on the recognized condition of the diffused layer.

Thus, with the evaluation method for a polycrystalline silicon film, since evaluation of a polycrystalline silicon film formed on a silicon film is performed by performing measurement of a diffused layer formed by diffusion of an impurity from the polycrystalline silicon film, the film quality of the polycrystalline silicon film can be evaluated without performing a complicated step (evaluation using a transmission electron microscope or the like) or a long or time-requiring step (production, measurement of a characteristic and so forth of a transistor). Consequently, film quality control of a polycrystalline silicon film can always be performed on a manufacture line.

Further, different from the conventional evaluation method, evaluation of a polycrystalline silicon film is performed but not indirectly using a transistor after production of the transistor is completed. Consequently, the condition of a polycrystalline silicon film can be evaluated in a condition wherein an influence of any other step is eliminated to the utmost.

The above and other objects, features and advantages of the present invention will become apparent from the following description and the appended claims, taken in conjunction with the accompanying drawings in which like parts or elements are denoted by like reference characters.

DESCRIPTION OF THE PREFERRED EMBODIMENTS

First Embodiment

Figure 1A:
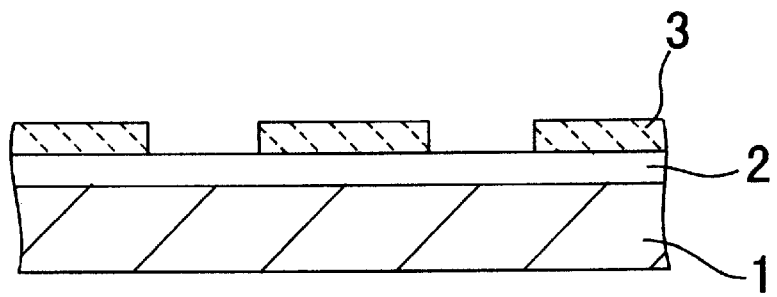
FIGS. 1(a) to 1(d) and 1(e) are schematic sectional views and a plan view illustrating different steps of an evaluation method for a polycrystalline silicon film to which the present invention is applied.
Figure 1B:
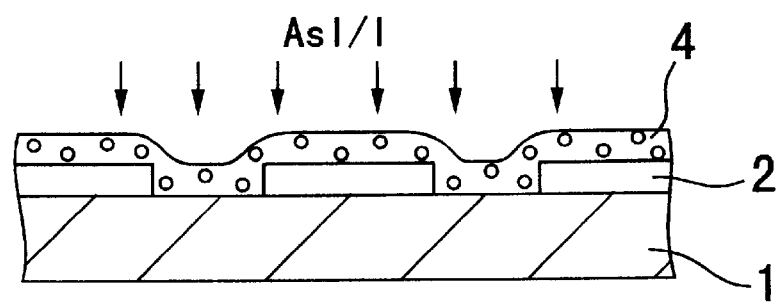
Figure 1C:
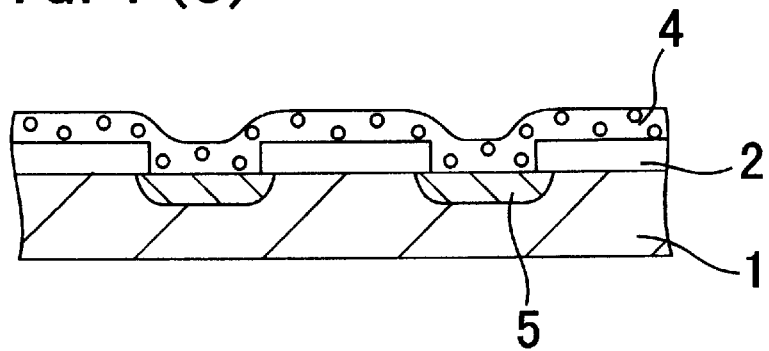

Referring first to FIGS. 1(a) to 1(d), there are shown sectional views of different successive steps of an evaluation method for a polycrystalline silicon film to which the present invention is applied. First, as shown in FIG. 1(a), a silicon oxide film 2 is formed on a p-type silicon substrate 1 using a thermal oxidation method or a CVD method, and a photo-resist film 3 having two openings therein is formed using a photo-lithography method. Then, as shown in FIG. 1(b), the silicon oxide film 2 is selectively etched using a wet or dry etching method to form two adjacent openings in the silicon oxide film 2, and then the photo-resist film 3 is removed. Thereafter, a polycrystalline silicon film 4 is grown, and an n-type impurity such as, for example, arsenic is implanted into the polycrystalline silicon film 4 by an ion implantation method. Where the silicon substrate used is otherwise of the n type, a different impurity such as boron is used. Thereafter, as seen from FIG. 1(c), the impurity in the polycrystalline silicon film 4 is diffused into the p-type silicon substrate 1 by heat treatment to form a diffused layer 5. If the ion implantation conditions and the heat treatment conditions are kept fixed, then the manner in which the impurity is diffused into the p-type silicon substrate 1 depends upon the film quality of the polycrystalline silicon film 4 and the interface condition between the polycrystalline silicon film 4 and the p-type silicon substrate 1.

Figure 1D:
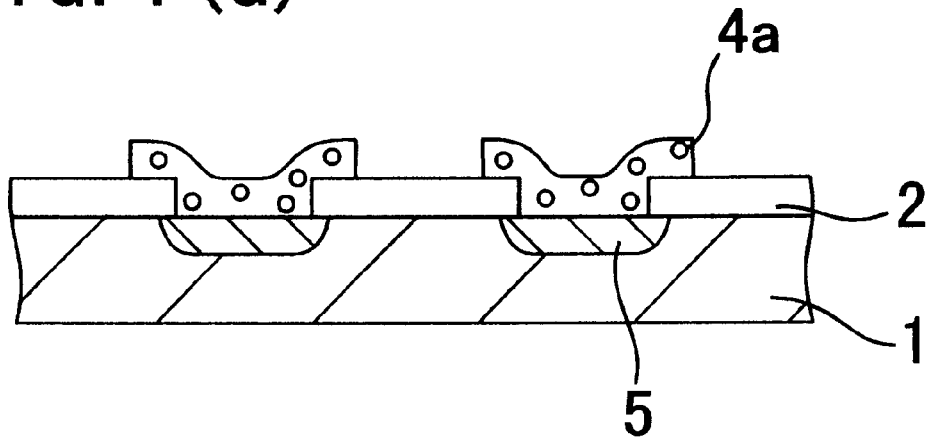
Figure 1E:
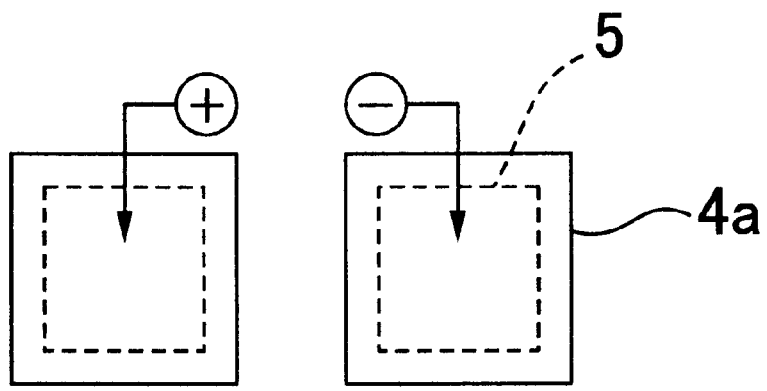

Then, as shown in FIG. 1(d), the polycrystalline silicon film 4 is patterned using a photo-lithography method and a dry etching method and so forth to form polycrystalline silicon electrodes 4a. A plan view of the product obtained in FIG. 1(d) is shown in FIG. 1(e). Then, a voltage is applied between the two electrodes 4a to measure a withstanding voltage of the product. The withstanding voltage varies in accordance with the extent of the diffused layer 5 which varies depending upon the film quality of the polycrystalline silicon film 4 and the interface condition between the polycrystalline silicon film 4 and the p-type silicon substrate 1.

If a correlation of the growth conditions, crystal particle sizes and so forth of the polycrystalline silicon film 4 to the withstanding voltage is taken, then the film quality and the interface condition of the polycrystalline silicon film can be evaluated only by measuring the polycrystalline silicon film.

Second Embodiment

Figure 2A:
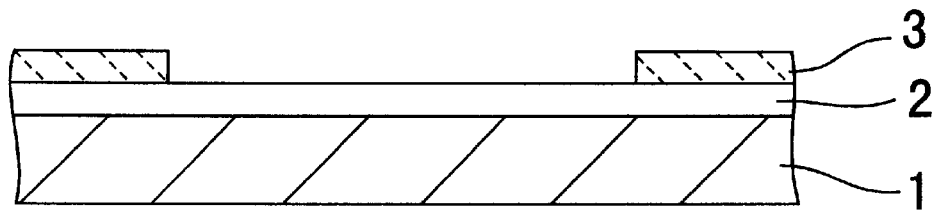
FIGS. 2(a) to 2(d) and 2e are schematic sectional views and a plan view illustrating different steps of another evaluation method for a polycrystalline silicon film to which the present invention is applied.
Figure 2B:
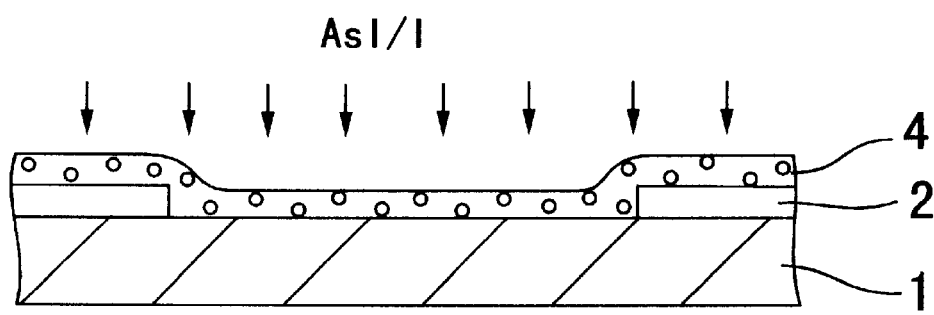
Figure 2C:
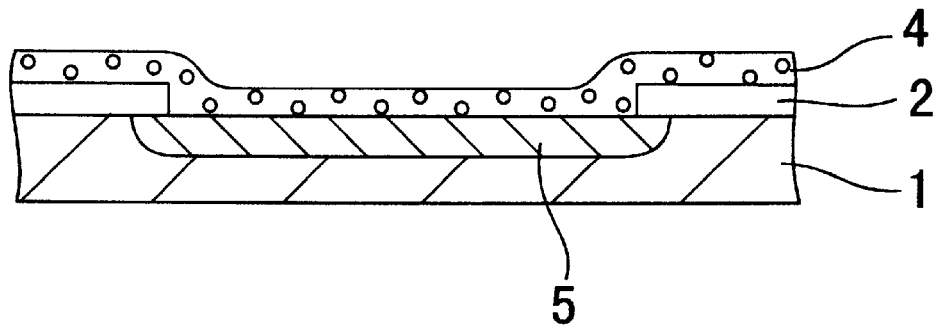

Referring now to FIGS. 2(a) to 2(d), there are shown sectional views of different successive steps of another evaluation method for a polycrystalline silicon film to which the present invention is applied. First, as shown in FIG. 2(a), a silicon oxide film 2 is formed on a p-type silicon substrate 1 using a thermal oxidation method or a CVD method, and a photo-resist film 3 having a rectangular opening therein is formed using a photo-lithography method. Then, as shown in FIG. 2(b), the silicon oxide film 2 is selectively etched using a wet or dry etching method to form a rectangular opening in the silicon oxide film 2, and then the photo-resist film 3 is removed. Thereafter, a polycrystalline silicon film 4 is grown, and an n-type impurity such as, for example, arsenic is implanted into the polycrystalline silicon film 4 by an ion implantation method. Thereafter, as seen from FIG. 2(c), the impurity in the polycrystalline silicon film 4 is diffused into the p-type silicon substrate 1 by heat treatment to form a diffused layer 5.

Figure 2D:
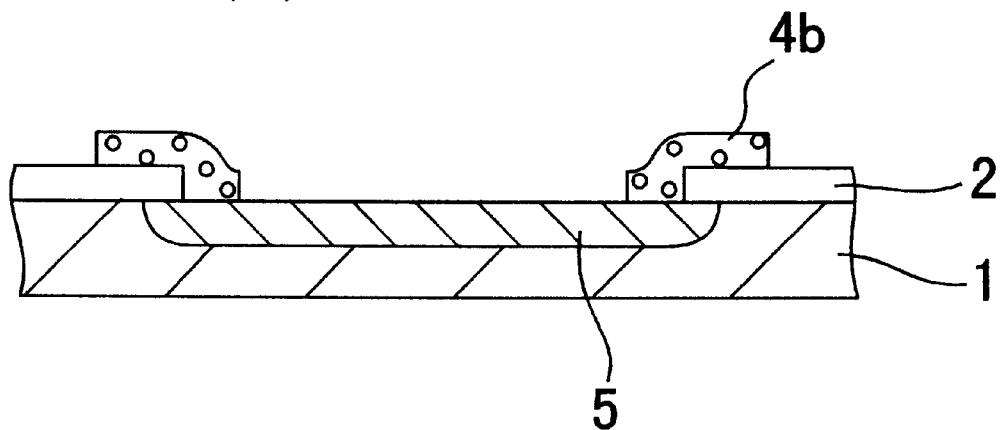
Figure 2E:
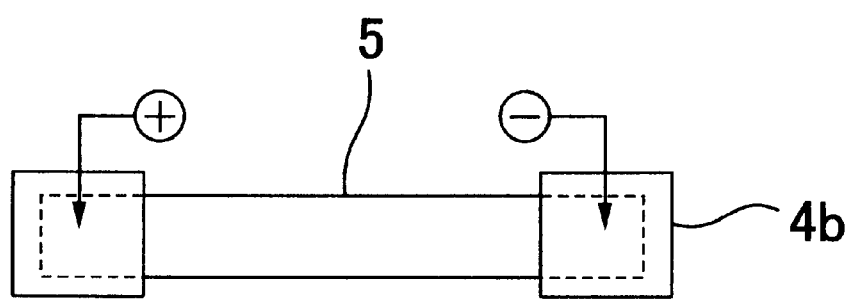

Then, as shown in FIG. 2(d), the polycrystalline silicon film 4 is worked using a photo-lithography method and a dry etching method so that it may overlap with the opposite ends of the diffused layer 5 to form two polycrystalline silicon electrodes 4b. A shape in plan of the product obtained in FIG. 1(d) is shown in FIG. 2(e).

Then, a voltage is applied between the two polycrystalline silicon electrodes 4b to measure a diffusion resistance of the product. Similarly as in the first embodiment described above, if the ion implantation conditions and the heat treatment conditions are kept fixed, then the diffusion resistance value depends upon the film quality of the polycrystalline silicon film 4 and the interface condition between the polycrystalline silicon film 4 and the p-type silicon substrate 1. If a correlation of the growth conditions, crystal particle diameters and so forth of the polycrystalline silicon film 4 to the resistance value is taken, then the film quality and the interface condition of the polycrystalline silicon film with the base can be evaluated only by measuring the polycrystalline silicon film.

It is to be noted that, for the method of doping an impurity into the polycrystalline silicon film 4 illustrated in FIG. 1(b) or 2(b), a thermal diffusion method can be used in place of an ion implantation method. In this instance, the impurity doping into the polycrystalline silicon film 4 illustrated in FIG. 1(b) or 2(b) and impurity diffusion into the silicon substrate illustrated in FIG. 1(c) or 2(c) may be performed by a single step.

Third Embodiment

Figure 3:
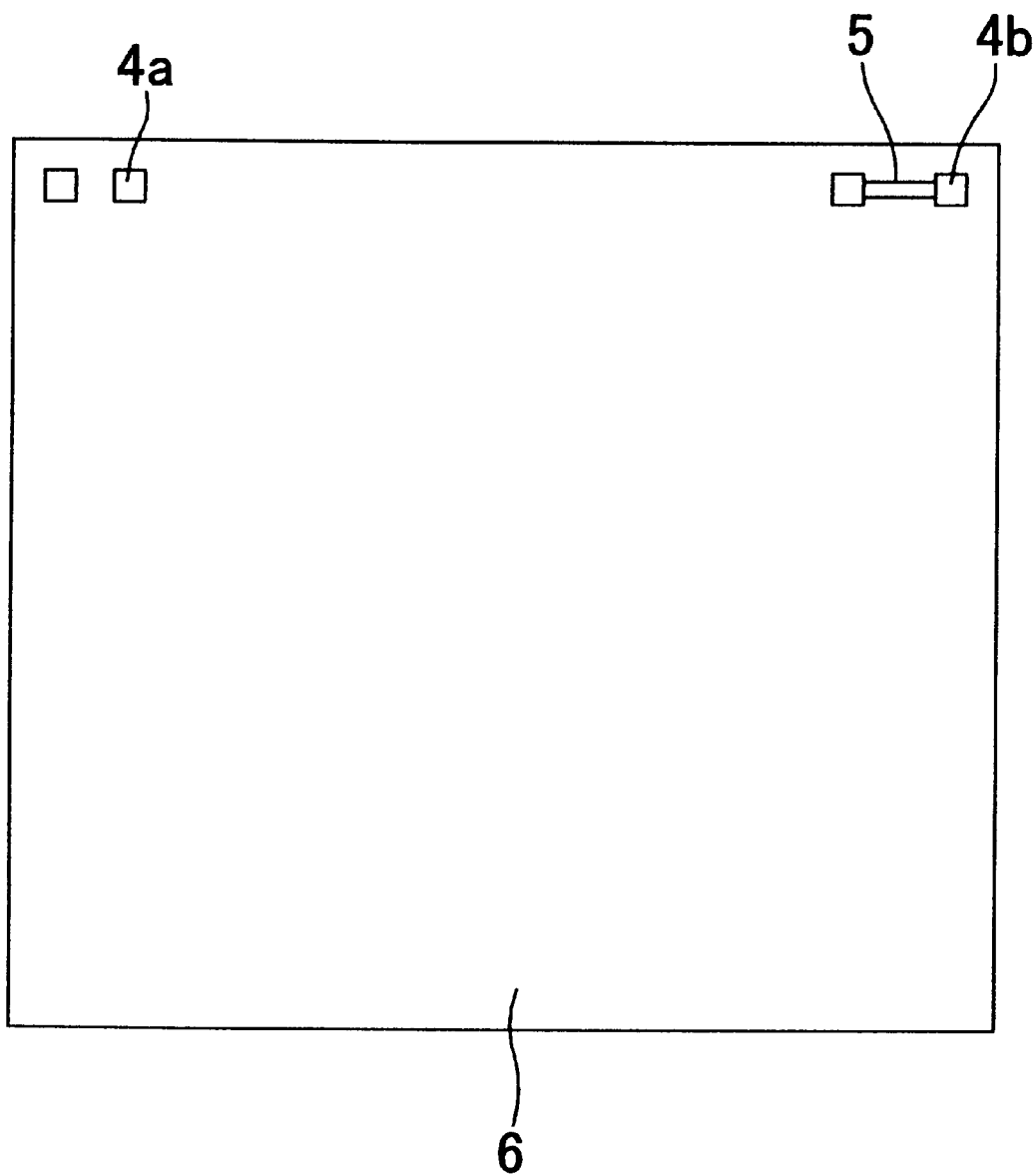
FIG. 3 is a plan view illustrating a further evaluation method for a polycrystalline silicon film to which the present invention is applied.
Figure 4A:
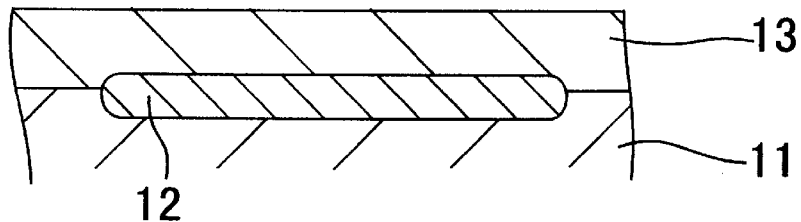
FIGS. 4(a) to 4(e) are schematic sectional views illustrating different steps of a conventional evaluation method for a polycrystalline silicon film.
Figure 4B:
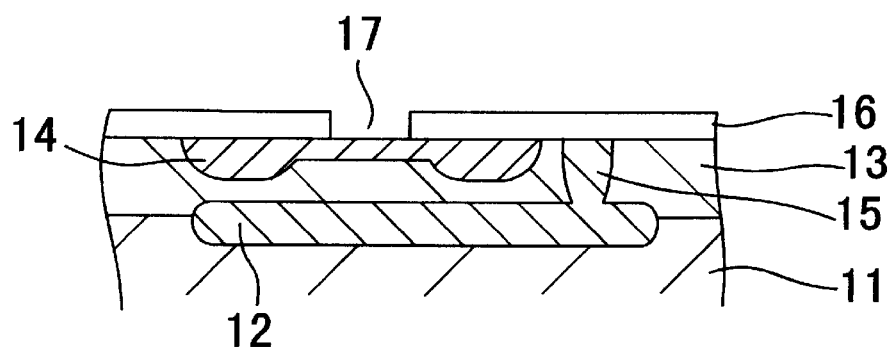
Figure 4C:
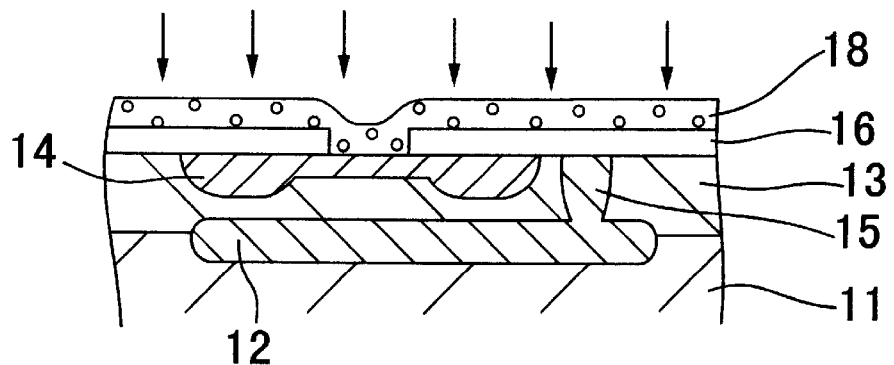
Figure 4D:
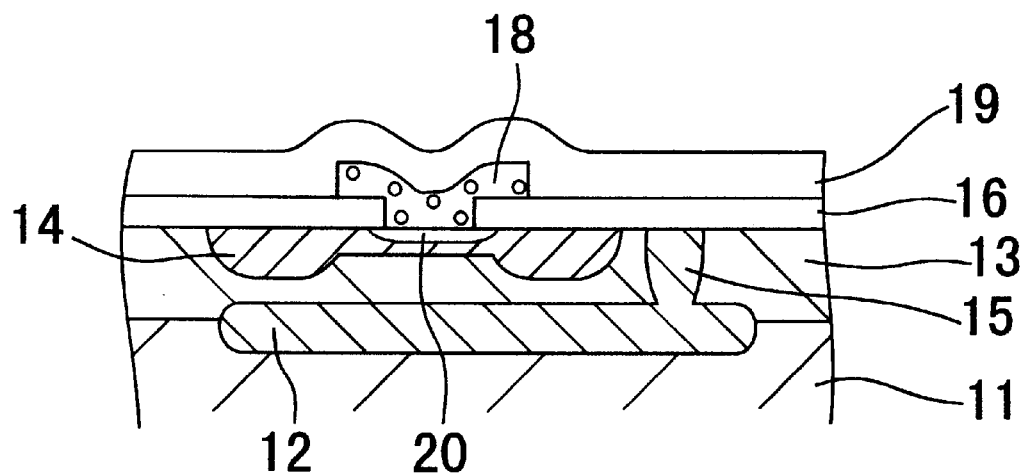
Figure 4E:
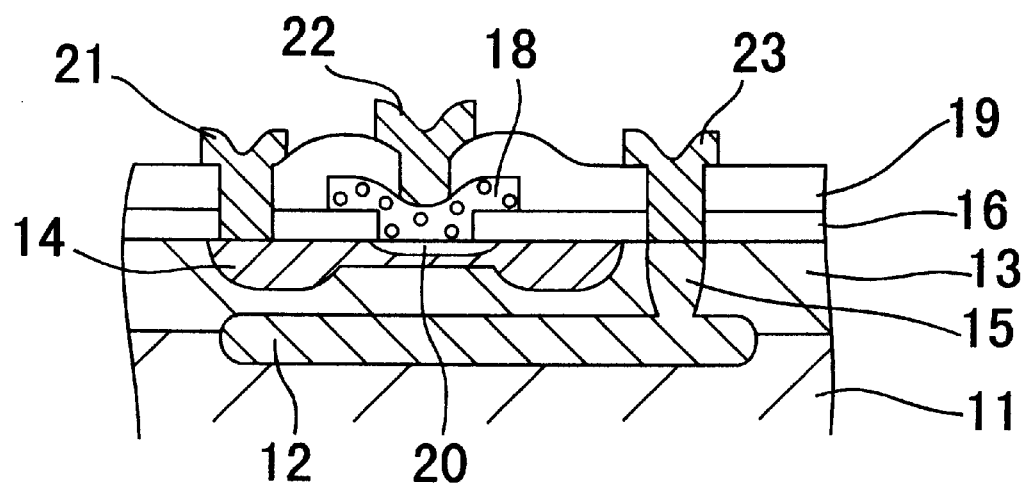

FIG. 3 is a plan view of a semiconductor chip (product chip) illustrating a further evaluation method for a polycrystalline silicon film to which the present invention is applied. Referring to FIG. 3, in the evaluation method of the present embodiment, two kinds of polycrystalline silicon film evaluation patterns including the evaluation pattern used in the first embodiment and the evaluation pattern used in the second embodiment are provided on a single semiconductor chip 6, and evaluation of a polycrystalline silicon film is performed using the patterns. Where one or a plurality of kinds of evaluation patterns are provided at a plurality of locations on the same chip or the same wafer and evaluation is performed for each of the regions of the evaluation patterns in this manner, evaluation with a higher degree of accuracy can be performed absorbing an influence of an in-plane dispersion.

In place of the evaluation patterns provided on the semiconductor chip 6, such evaluation patterns may be formed in regions in which a product chip is not to be formed such as on a scribe line. Where evaluation patterns are formed on a wafer on which product chips are formed as in the third embodiment described above, the operations in the steps described hereinabove with reference to FIGS. 1(a) to 1(d) and/or FIGS. 2(a) to 2(d) can be performed in a step for forming a semiconductor device. This allows evaluation of a polycrystalline silicon film without increasing the number of steps.

Having now fully described the invention, it will be apparent to one of ordinary skill in the art that many changes and modifications can be made thereto without departing from the spirit and scope of the invention as set forth herein.

What is claimed is:

1. An evaluation method for a polycrystalline silicon film, comprising:

a first step of forming an insulating film on a silicon substrate and forming an opening in the insulating film;

a second step of depositing a polycrystalline silicon film on the overall area of the insulating film and the silicon substrate;

a third step of doping the polycrystalline silicon film with an impurity and performing heat treatment to form a diffused layer in a surface region of the silicon substrate through the polycrystalline silicon film in the opening of the insulating film; and a fourth step of evaluating the diffused layer formed by the third step to evaluate a film quality of the polycrystalline silicon film in accordance with said impurity of said diffused layer.

2. An evaluation method for a polycrystalline silicon film as claimed in claim 1, wherein, after the third step, the polycrystalline silicon film is patterned to form a pair of electrodes which contact with the diffused layer, and in the fourth step, an electric resistance of the diffused layer is measured making use of the electrodes.

3. An evaluation method for a polycrystalline silicon film as claimed in claim 1, wherein, in the first step, a pair of openings are formed in the insulating layer, and after the third step, the polycrystalline silicon film is patterned to form a pair of electrodes which contact with different pieces of the diffused layer, and then in the fourth step, a withstanding voltage between the different pieces of the diffused layer is measured.

4. An evaluation method for a polycrystalline silicon film as claimed in claim 1, wherein the first to fourth steps are used also as steps of manufacturing a product chip, and the opening is formed on the product chip or a scribe line.

5. An evaluation method for a polycrystalline silicon film as claimed in claim 1, wherein openings of a same pattern or different patterns are formed in different regions on a single wafer, and a film quality of the polycrystalline silicon film is evaluated for the plurality of different regions.

6. An evaluation method for a polycrystalline silicon film, comprising:

a first step of forming an insulating film on a silicon substrate and forming an opening in the insulating film;

a second step of depositing a polycrystalline silicon film on the overall area of the insulating film;

a third step of doping the polycrystalline silicon film with an impurity and performing heat treatment to form a diffused layer in a surface region of the silicon substrate through the polycrystalline silicon film in the opening of the insulating film; and a fourth step of evaluating the diffused layer formed by the third step thereby to evaluate a film quality of the polycrystalline silicon film;

wherein, after the third step, the polycrystalline silicon film is patterned to form a pair of electrodes which contact with the diffused layer, and in the fourth step, an electric resistance of the diffused layer is measured making use of the electrodes.

* * * * *